(12) United States Patent
Le Bras

(10) Patent No.: US 9,119,555 B2
(45) Date of Patent: Sep. 1, 2015

(54) METHOD FOR CORRECTING AN ACQUIRED MEDICAL IMAGE AND MEDICAL IMAGER

(75) Inventor: Anthony Le Bras, Quimperle (FR)

(73) Assignee: EOS IMAGING, Paris (FR)

( * ) Notice: Subject to any disclaimer, the term of this patent is extended or adjusted under 35 U.S.C. 154(b) by 597 days.

(21) Appl. No.: 12/666,406

(22) PCT Filed: Jul. 4, 2007

(86) PCT No.: PCT/IB2007/053434
§ 371 (c)(1),
(2), (4) Date: Dec. 23, 2009

(87) PCT Pub. No.: WO2009/004410
PCT Pub. Date: Jan. 8, 2009

(65) Prior Publication Data
US 2010/0177948 A1    Jul. 15, 2010

(51) Int. Cl.
| | | |
|---|---|---|
| G06K 9/00 | (2006.01) | |
| A61B 6/08 | (2006.01) | |
| A61B 5/107 | (2006.01) | |
| A61B 6/04 | (2006.01) | |
| A61B 6/06 | (2006.01) | |
| A61B 6/00 | (2006.01) | |

(52) U.S. Cl.
CPC ............ *A61B 6/08* (2013.01); *A61B 5/1075* (2013.01); *A61B 6/04* (2013.01); *A61B 6/06* (2013.01); *A61B 6/4014* (2013.01); *A61B 6/4441* (2013.01); *A61B 6/463* (2013.01); *A61B 6/588* (2013.01); *A61B 6/505* (2013.01)

(58) Field of Classification Search
CPC ............ G01N 21/6458; G01N 2015/1479; G01N 2015/1497; G01N 15/1475; G01N 23/20; G01N 27/3275; G06K 7/14; G06K 7/1465; G06K 7/1491; G06K 9/00664; G06K 9/036
USPC ................................................ 382/132, 131
See application file for complete search history.

(56) References Cited

U.S. PATENT DOCUMENTS

| | | | |
|---|---|---|---|
| 5,959,302 A | | 9/1999 | Charpak |
| 5,970,119 A | * | 10/1999 | Hofmann ...................... 378/163 |
| 7,907,765 B2 | * | 3/2011 | Fauver et al. ................. 382/131 |

(Continued)

FOREIGN PATENT DOCUMENTS

| | | |
|---|---|---|
| EP | 1168249 A1 | 1/2002 |
| EP | 1417931 A1 | 5/2004 |

(Continued)

OTHER PUBLICATIONS

International Search Report of PCT/IB2007/053434; May 19, 2008; Pau Montes.

(Continued)

*Primary Examiner* — Maroun Kanaan
(74) *Attorney, Agent, or Firm* — BCF LLP

(57) ABSTRACT

Method for correcting an acquired medical image of a patient showing a representation of an internal body structure, the acquired image having been acquired in a medical imager having a radiation source and a radiation detector spaced from one another along an image-taking direction, and between which the patient is disposed. One obtains, from the acquired image, a corrected image taking into account a position of the internal body structure along the image-taking direction.

26 Claims, 6 Drawing Sheets

(56) References Cited

U.S. PATENT DOCUMENTS

2002/0141540 A1    10/2002  Vaillant et al.
2005/0074088 A1*  4/2005  Ichihara et al. ................ 378/58
2008/0063304 A1*  3/2008  Russak et al. ................ 382/298

FOREIGN PATENT DOCUMENTS

FR        2749402 A1    12/1997
FR        2754068 A1    4/1998

OTHER PUBLICATIONS

English abstract of FR2749402.
English abstract of FR2754068.
English Abstract of EP1168249.
Office Action dated Oct. 4, 2010; issued by the European Patent Office for European Patent Application No. 07 826 154.2 filed Jul. 4, 2007.
Response dated Mar. 14, 2011 to Office Action dated Oct. 4, 2010 for European Patent Application No. 07 826 154.2 filed Jul. 4, 2007.

* cited by examiner

METHOD FOR CORRECTING AN ACQUIRED MEDICAL IMAGE AND MEDICAL IMAGER

FIELD OF THE INVENTION

The instant invention relates to methods for correcting an acquired medical image and to medical imagers.

BACKGROUND OF THE INVENTION

In particular, the instant invention is related to a method for correcting an acquired medical image of a patient having an internal body structure, said acquired image having a region of interest showing a representation of said internal body structure, said acquired image having been acquired in a medical imager having a radiation source and a radiation detector spaced from one another along an image-taking direction, and between which the patient is disposed.

In planar imaging, there always is a magnification depending on the geometry of the radiation beam emitted by the source, the mode of projection and the position of the patient and/or the position of the region of interest inside the patient. Radiologists and orthopaedists are used to make some measurements on radiographs. However, most of the time, these measurements are approximate because the clinicians do not know accurately the factor of magnification associated with the radiographs. In fact, as the radiologist technician does not know accurately the position of the patient in the depth of the beam, he cannot provide accurately the magnification factor associated with the image.

Thus, when a radiologist wants to have an accurate measurement for a specific body part of the patient, he usually puts spherical beads (or another type of landmarks) of known dimensions on the external surface of the patient, approximately close to the location of the internal body part. Correlation between the known size of the bead and the size of the image of the bead provide the magnification factor at the external surface of the patient close to the specific body part.

However, the use of landmarks shows limitations. Positioning landmarks is time consuming, and is sometimes unpleasant for the patient (these landmarks being sometimes located near intimate parts of the body). Further, the landmarks will only provide the magnification factor at the external surface of the patient, which might be far away from the internal body part, in particular, but not only, for obese patients.

For all these reasons, one strives to limit the use of landmarks for correcting the magnification factor of a medical imager.

SUMMARY OF THE INVENTION

To this aim, according to the invention, such a method is characterized in that it comprises:

(a) obtaining, from the acquired image, a corrected image taking into account a position of the internal body structure along the image-taking direction.

By using the position of the internal body structure along the image-taking direction, rather than the position of the external surface of the patient close to the internal body structure, the factor to be applied in order to correct magnification issues associated with the acquisition is known with more accuracy, and accurate images will be provided, which might be the basis for a diagnostic or a quantitative measurement.

In some embodiments, one might also use one or more of the features as defined in the dependant claims.

In particular, a positioning device can be used for obtaining the position of the internal body part. The position of the positioning device, along the image-taking direction, is well-referenced in the frame of reference of the medical imager, for example by construction of the medical imager, because the positioning device is part of, or a movable part of the imager.

BRIEF DESCRIPTION OF THE DRAWINGS

Other characteristics and advantages of the invention will readily appear from the following description of one of its embodiments, provided as a non-limitative example, and of the accompanying drawings.

On the drawings.

On the different Figures, the same reference signs designate like or similar elements.

DETAILED DESCRIPTION

Figure 1:
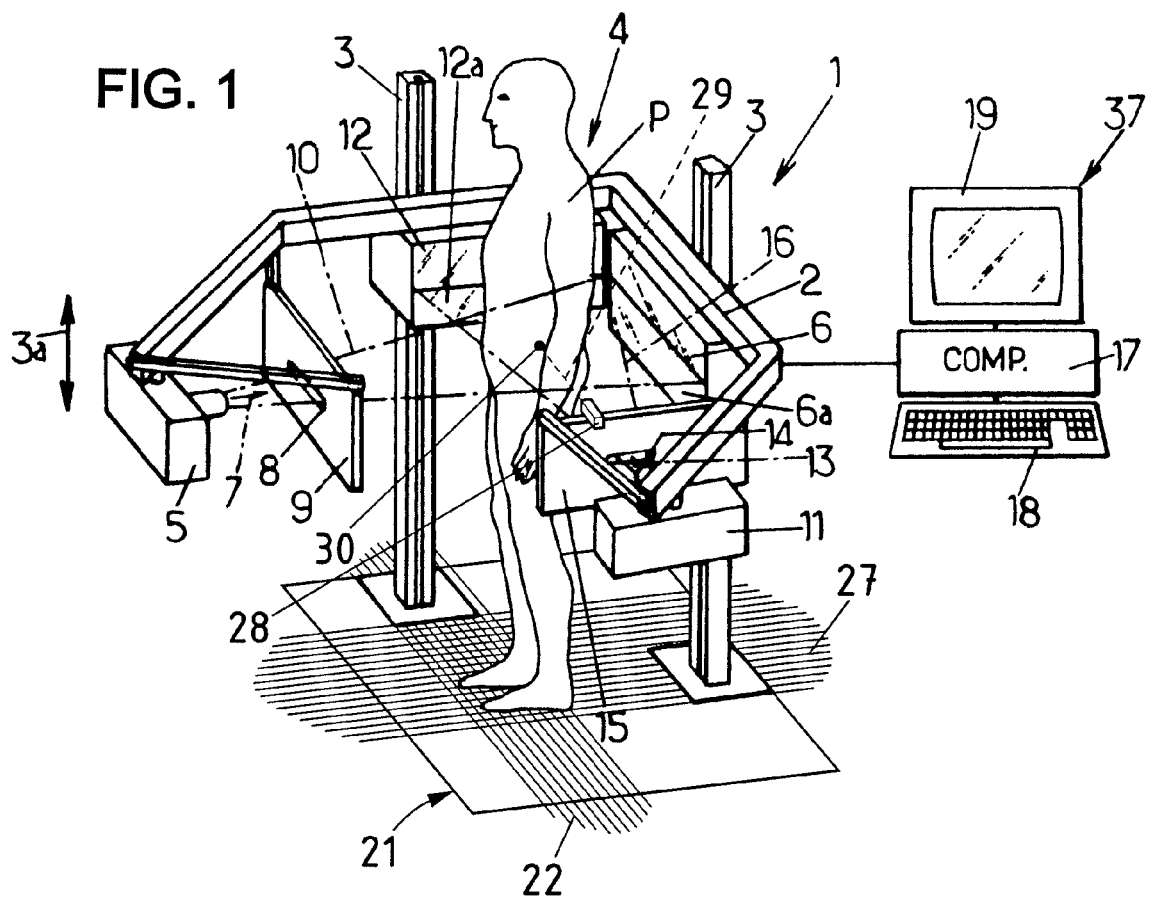
FIG. 1 is a perspective view of a medical imager.

FIG. 1 shows a medical imager 1 such as a radiographic apparatus, the apparatus comprising a moving frame 2 displaceable under motor drive along vertical guides 3 in both directions of translation 3a.

The frame surrounds a field of observation 4 in which a patient P can be placed, e.g. standing, for observing an osteo-articular structure of the patient when in the standing position, which can be important for patients suffering from scoliosis, for example.

The moving frame 2 carries a first radiological source 5 and a first detector 6 which is placed facing the source 5 beyond the field 4, and which comprises at least one horizontal line 6a of detector cells. By way of example, the detector 6 may be a gas detector responsive to low doses of radiation, e.g. as described in documents FR-A-2 749 402 or FR-A-2 754 068. Naturally, other types of detectors may optionally be used in the context of the present invention.

The radiological source 5 is adapted to emit ionizing radiation, in particular X-rays, suitable for being detected by the detector 6 in a first image-taking direction 7 that is antero-posterior relative to the patient P, the rays passing through a horizontal slit 8 made through an aiming mask 9 such as a metal plate in order to generate a horizontal beam 10 of ionizing radiation in the field of observation 4.

The moving frame 2 also carries a second radiological source 11 similar to the source 5 and a second detector 12 similar to the detector 6, disposed facing the source 11 beyond the field 4, and comprising at least one horizontal line 12a of detector cells.

The radiological source 11 is adapted to emit ionizing radiation in a second image-taking direction 13 that is lateral relative to the patient P, passing through a horizontal slit 14 formed in an aiming mask 15 such as a metal plate in order to generate a horizontal beam 16 of ionizing radiation in the field of observation 4.

Naturally, there could be more than two radiological sources and detectors, and the image-taking directions of these various radiological sources could, where appropriate, be other than mutually perpendicular, and they need not even be horizontal.

The two detectors 6, 12 are connected to a computerized system 37 or some other electronic control system fitted with:
- an input interface comprising at least a keyboard 18 and generally also a mouse (not shown);
- an output interface comprising at least a screen 19;
- a processor 17 for executing a computer program adapted to implement the method described herein.

The microcomputer 37 may also be connected to the motor-driven drive means (not shown) contained in the guide 3, and to the sources 5 and 11, so as to control vertical displacement of the frame and the emission of ionizing radiation.

The medical imager further comprises a positioning device for detecting a position of an internal body structure of the patient. The nature of the positioning device could vary, and three different embodiments are described here. Although the three different embodiments are represented on the same medical imager, it is understood that a medical imager could comprise only one, or two of these (or other) positioning devices.

According to a first embodiment, the positioning device comprises the second source 11 and detector 12 themselves, as will be explained in detail below, and is used for detecting the position of the internal body structure along the first image-taking direction.

According to a second embodiment, the positioning device comprises a calibrated grid 21 which is drawn, for example on the floor of the imager. The grid 21 comprises for example one first set of parallel lines 22, perpendicular to the first image-taking direction, and equally spaced from each other, for example by a given distance. These lines will be referenced in the frame of reference of the imager. For example, the distance from each line to a reference line corresponding to the position of the first source 5 along the first image-taking direction is known by construction of the imager.

Visual inspection by the practitioner will enable to determine the position of the internal body structure of interest. By using anatomical knowledge, the practitioner can evaluate the approximate position of the internal body structure of interest. By drawing a vertical line passing through this estimated position, the crossing of the vertical line with one line of the first set of lines 22 will provide the position of the internal body structure along the first image-taking direction. This position can be recorded in the computer by the practitioner, for example with the keyboard. He can input different position values for different body structures.

Possibly, the floor grid 21 will comprise a second set of lines extending parallel to each other, and perpendicular to the second image-taking direction, and referenced with respect to a line corresponding to the second source 11, which enable to define a position along the second image-taking direction with respect to the second source 11.

According to a third embodiment, the positioning device comprises an auxiliary emitter 28, such as a LASER or else, able to emit a visible beam 29 which will provide a visible spot 30 on the external surface of the patient. The auxiliary emitter 28 is carried by the structure of the imager, with a known position with respect to the structure of the imager along the first image-taking direction. The orientation of the LASER with respect to the first image-taking direction is fixed, and the LASER is translatable, by motorized means, with respect to the structure of the medical imager, along the first image-taking direction. Also, the LASER might be rotatable about the first image-taking direction to sweep along the height of the patient.

By using for example the input means of the computer 37, using anatomical knowledge, a practitioner will move the LASER beam 24 until the LASER spot will point directly on the internal body structure. The position of the LASER along the first image-taking direction at that time is well known and can be recorded inside the computer.

This lateral position will be used for correcting the frontal image. A similar LASER could be used to determine a frontal position of an anatomical structure of the patient for correcting the lateral image.

The above-described apparatus operates as follows:

The microcomputer 37 is used initially to take two radiographic images of the patient P by causing the field of observation 4 to be scanned by the beams 10 and 16 of ionizing radiation over a height corresponding to the structure of the patient that is to be observed, for example the spine and the pelvis, or indeed the entire skeleton. For this purpose, the frame is preferably displaceable over a height of not less than 70 centimeters (cm), and preferably over at least one meter.

Figure 2A:
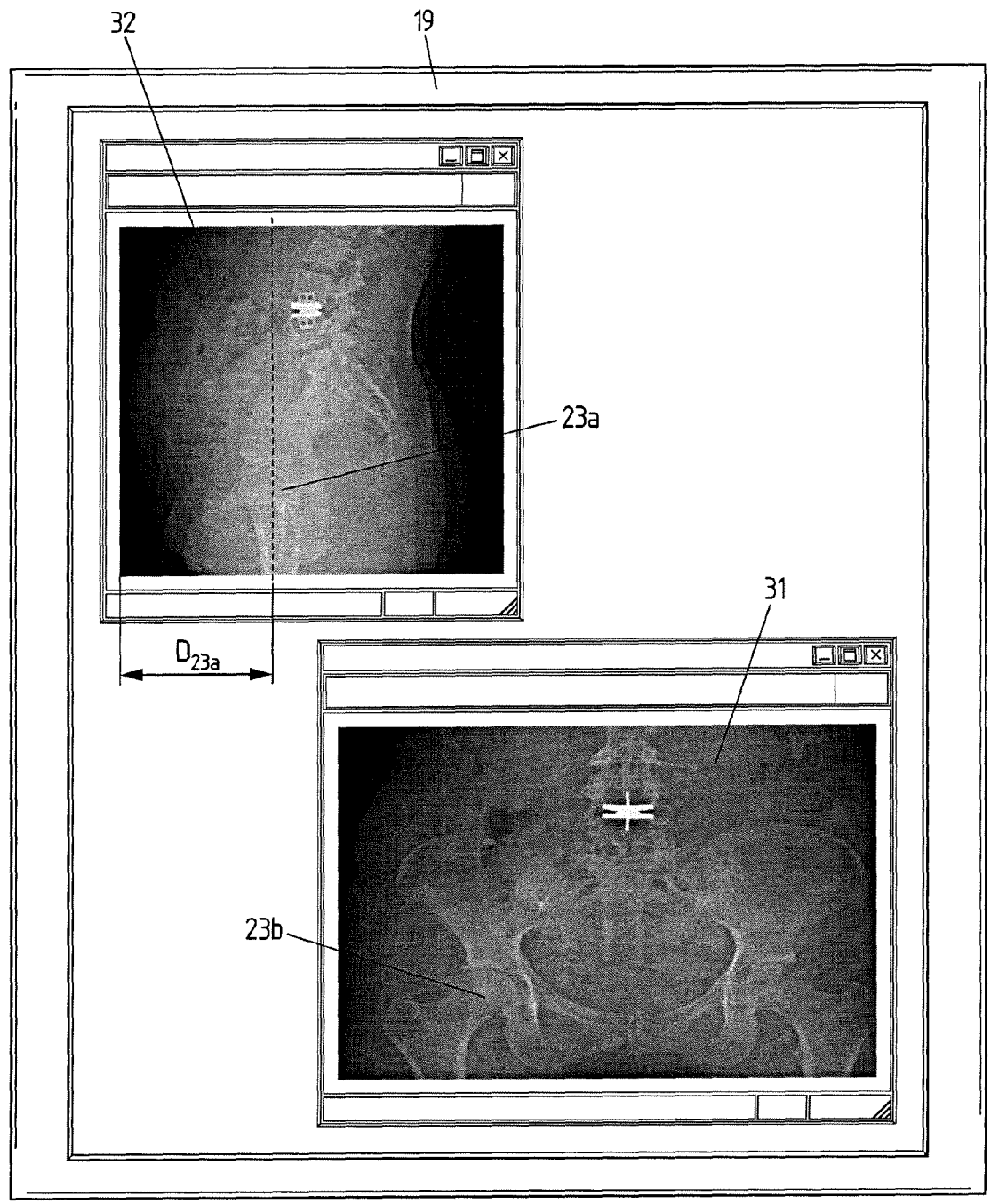
FIG. 2a is a view of the acquired images on the display screen of FIG. 1.

During this movement, two calibrated digital radiographic images of the portion of the patient under examination are stored in the memory of the microcomputer 37, for example an antero-posterior image 31 and a lateral image 32 respectively, which images can be viewed on the screen 19 of the microcomputer, as shown in FIG. 2a.

These images are directly calibrated, since the source-to-detector distance is well known and fixed by construction of the medical imager. Thus, the bi-dimensional coordinates of a pixel of the detector (image frame of reference) are directly related to its tri-dimensional coordinates in the imager's frame of reference.

Figure 5A:
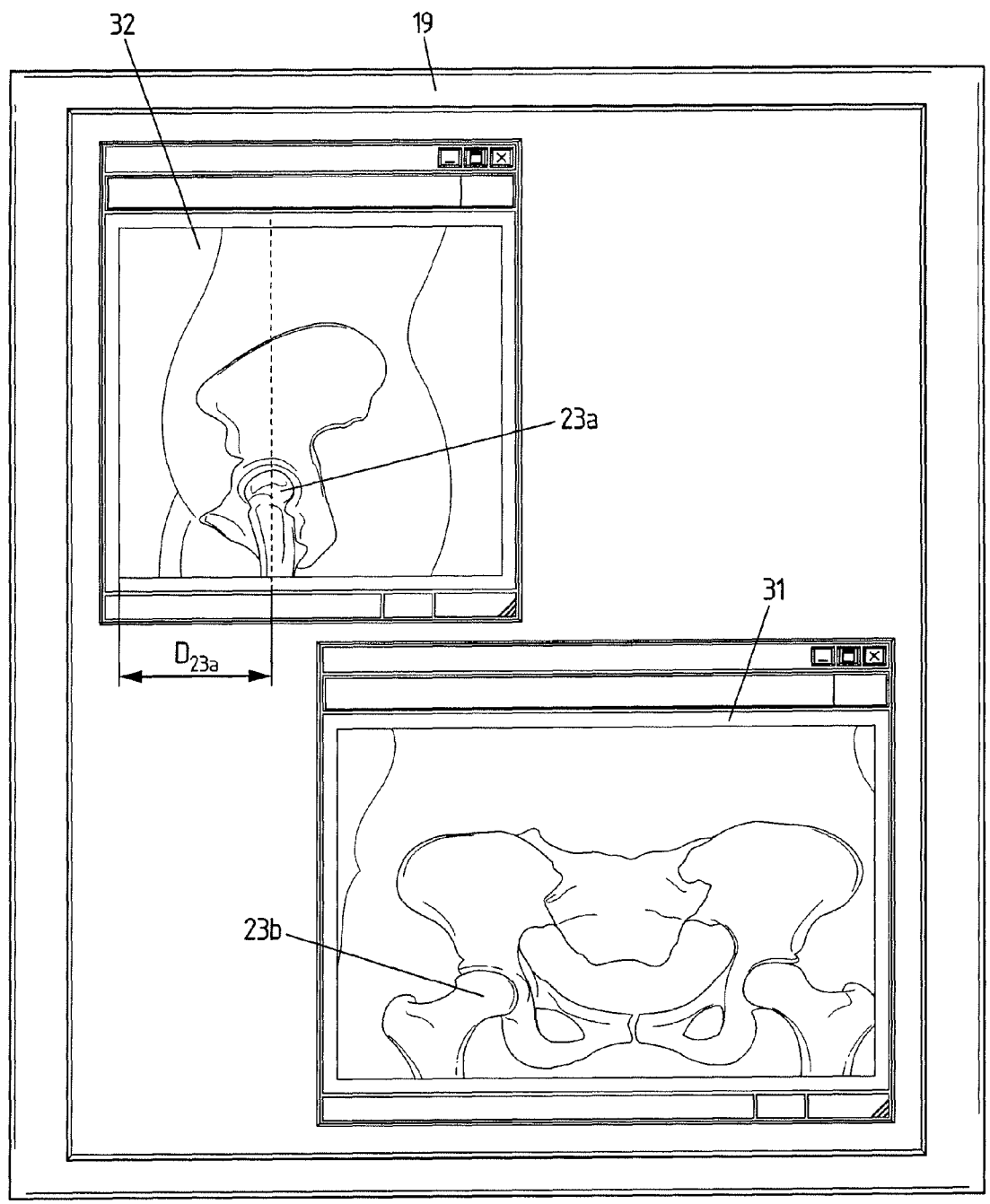
FIGS. 5a, 5b are schematic views corresponding to FIGS. 2a, 2b respectively.

Bi-dimensional detection data of the structure, such as an antero-posterior and a lateral radiographs obtained by the apparatus of FIG. 1, is displayed on a screen 19 of the computerized system 37 as shown on FIG. 2a. FIG. 2a shows the real detection data obtained with the image, and FIG. 5a is a schematic representation of the anatomical features of interest, FIG. 5a being for explanatory purposes for the present application, but not obtained by the medical imager itself. It should be understood that detection data such as the radiographs of FIG. 2a, do not necessarily provide with such a clear representation of the structure as shown on FIG. 5a. Representations (projections) of an internal body structure (for example the left femoral head 23) of the patient are identified by reference number 23b on the frontal image (right side of FIG. 2a), and 23a on the lateral image (left side of FIG. 2a).

The frontal image 31 will now be corrected by using the position information obtained by the positioning device. For example, the frontal image 31 will be corrected so that the left femoral head 23 (identified by its representation 23a, 23b on the images) is accurately resized.

According to the first embodiment, the position of the image of the left femoral head in the second image 32 is determined, either manually by the practitioner or automatically by image processing. A distance $D_{23a}$ from the centre of the image of the object to the edge of the image can be measured. Since the spatial relationship of the edge of the image acquired by the second detector to the first source and the first detector are known by the construction of the imager, this will provide the position of the image of the object along the first image-taking direction in the imager's frame of reference.

The position of interest for the object itself with reference to the source 5 along the first image-taking direction can be estimated from $D_{23a}$. It could be simply interpolated in view of the global position of the body along the second image-taking direction, or more accurately using the first image 31 to estimate where, along the line joining point 23a to the source 11, the left femoral head is located.

Figure 4:
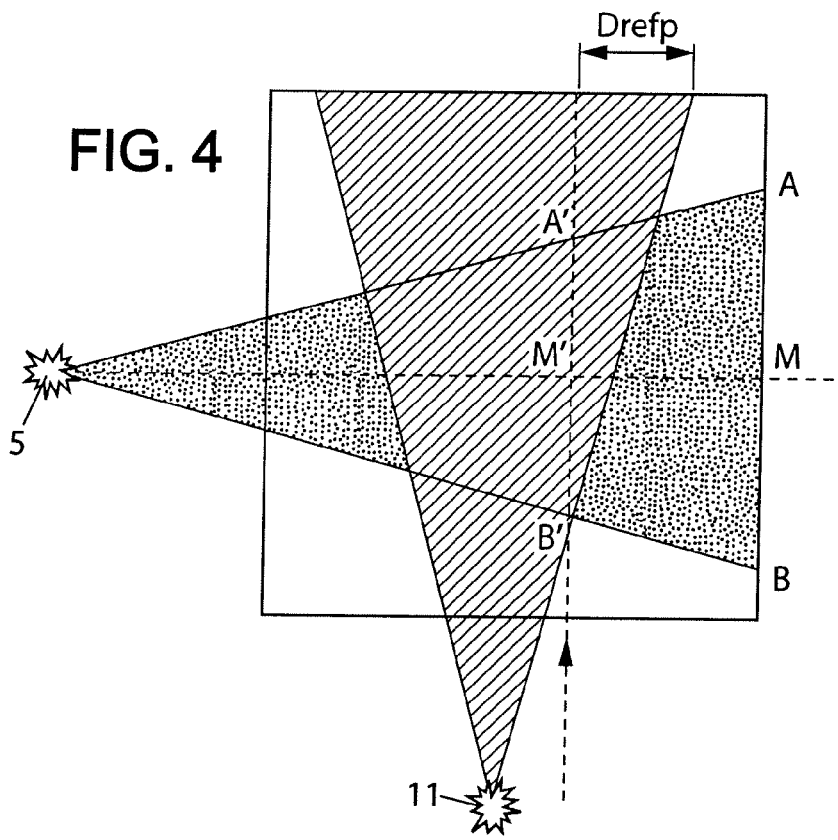
FIG. 4 is a schematic top view corresponding to the view of FIG. 3.

The position is used for resizing the image. As is known from the Thalès formula (see FIG. 4):

$$O_2M'/O_2M = A'B'/AB,$$

where $O_2$ is the source 5, M' is the middle position of the internal body structure, M is the image of the middle position of the internal body structure, AB is the width of the detector, and A'B' is the width of the part of the patient at the level of M' which can be visualized by the detector.

Figure 2B:
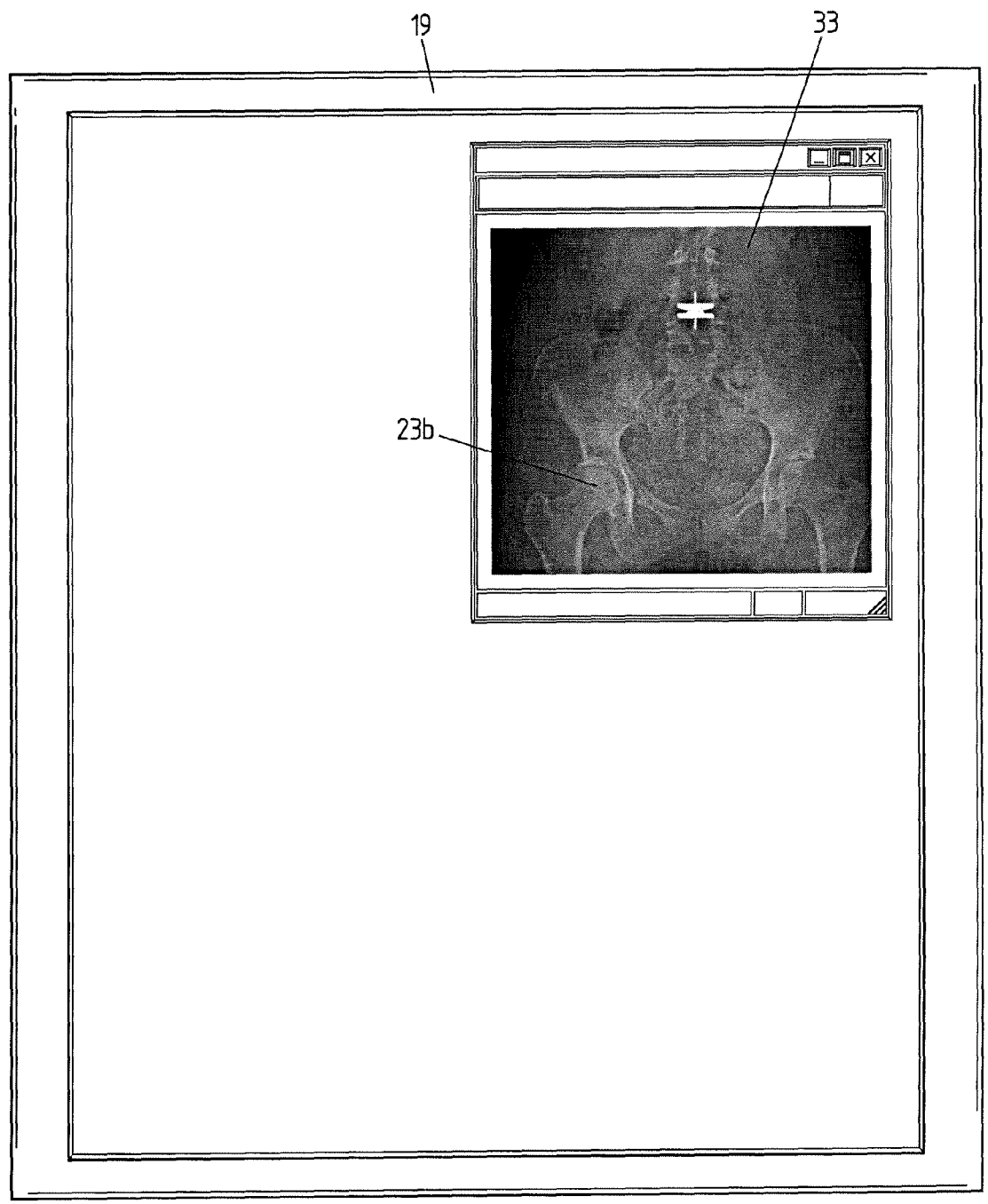
FIG. 2b is a view of one of the images of FIG. 2a after correction.
Figure 3:
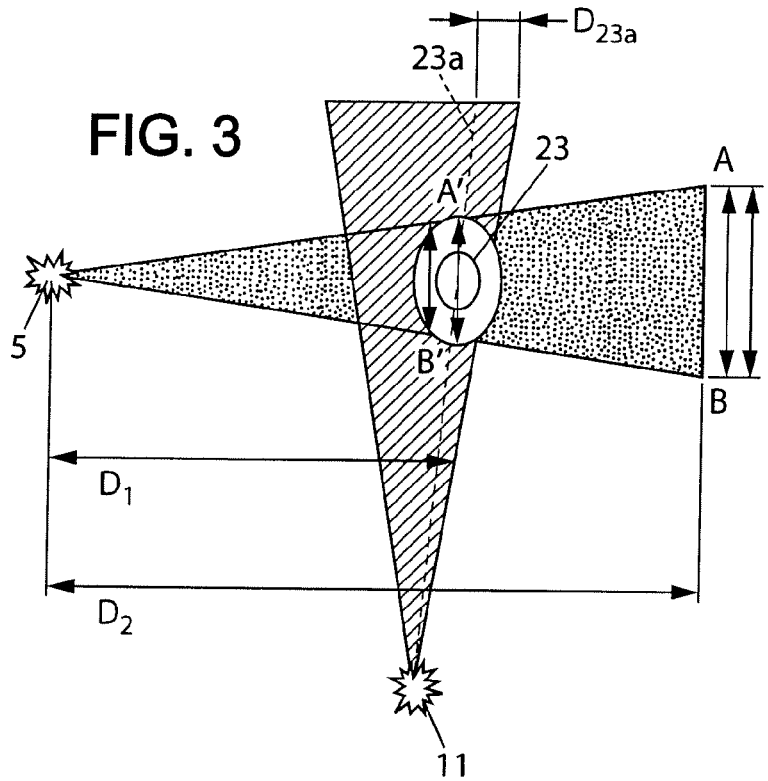
FIG. 3 is a schematic top view of the apparatus of FIG. 1.
Figure 5B:
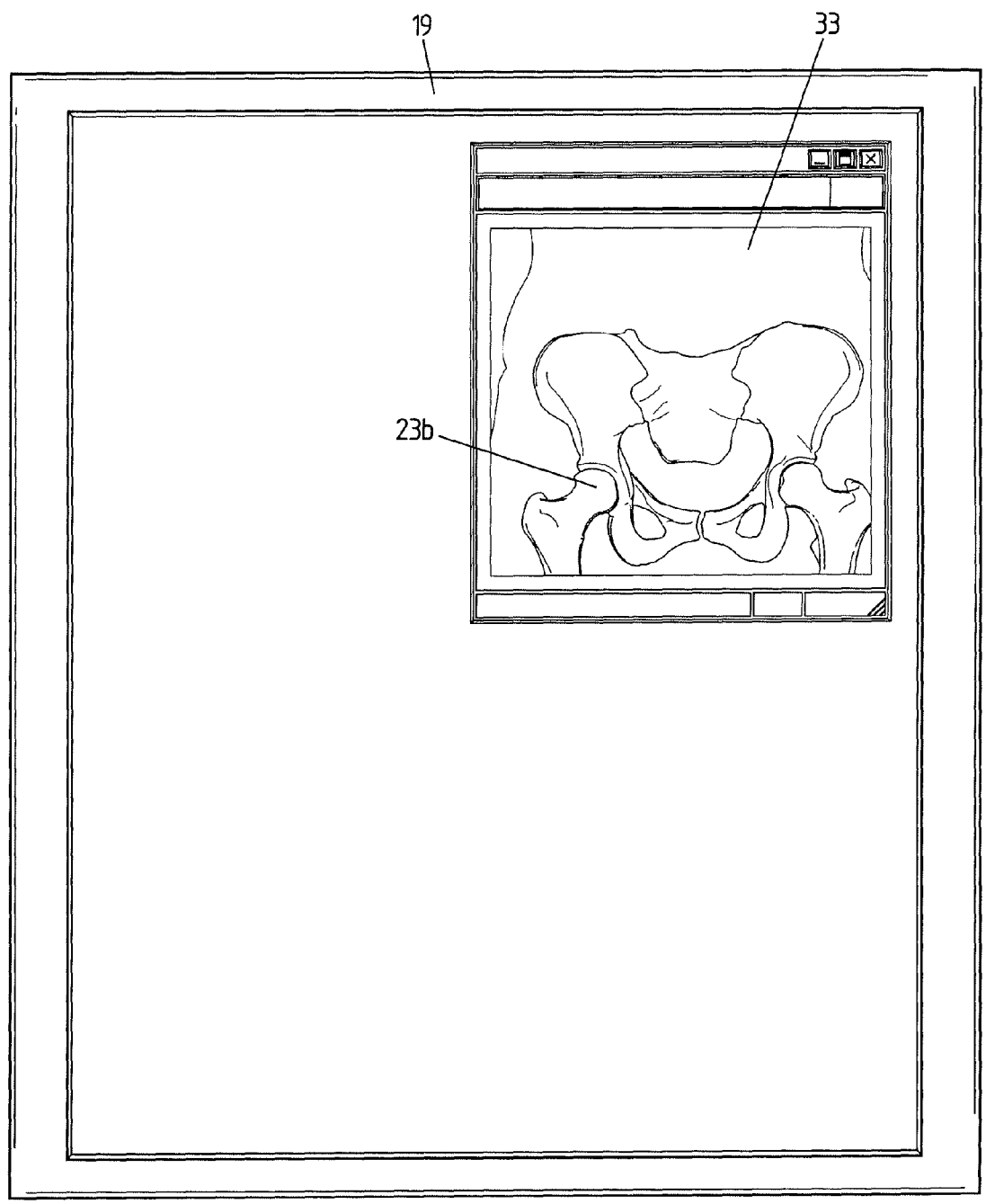

AB is known from the size of the detector, $O_2M$ is known from the source-to-detector distance, and $O_2M'$ is known from the above-calculated position (by either of the mentioned-methods, alone or in combination). Knowing AB, $O_2M$ and $O_2M'$, the Thales formula enables to calculate the real distance A'B', hence the magnification factor for this depth (position along the first image-taking direction) of the image. The corrected image 33 is shown on FIG. 2b (or schematic representation on FIG. 5b).

Further, different corrected images could be obtained, for different anatomical features of interest having different positions along the first image-taking direction.

Furthermore, it should be noted that, since the lateral image provides anatomical objects which are at different positions along the first image-taking direction, it is possible to vertically deal the first image in different regions of interest, each comprising an anatomical objects of interest, and to apply a different magnification factor for each region of interest, each corresponding to the corresponding position along the first image-taking direction of the given anatomical object. This would provide an image for which the magnification would be correct for all the anatomical objects of interest.

The corrected image can be used by a clinician in a measuring method, whereby a geometrical parameter (length, radius, angle) of an internal body structure is accurately measured on the corrected image(s). This parameter could be used for establishing a diagnostic.

Of course, in the case of the apparatus of FIG. 1, the same method can be implemented for the second image 32, whereby the lateral position of the femoral head is estimated from the first image 31 for providing a correctly magnified image from the second image 32.

The two obtained images can then be used in a three-dimensional reconstruction method, whereby a three-dimensional model, obtained from a previously-acquired knowledge base of similar vertebra, for example memorized in the computer, is placed and sized so as to best fit with the corrected images.

With the medical imager which has been described, the acquisition is performed by a fan beam, so that magnification correction need to be performed only on the image's width.

The invention could be implemented in a medical imager which does not necessarily use fan-beam acquisition. It is understood that, in case of cone beam acquisition, the obtained magnification correction factor will be used for correcting the image along its both dimensions by an equal correction factor.

The present invention has been presented with an embodiment which simultaneously acquires two orthogonal images by scanning. Simultaneous acquisition ensures that the patient will not have moved between the antero-posterior and the lateral acquisitions.

Yet, it is not compulsory for the invention that the two images will be orthogonal, nor that they will be acquired simultaneously, nor by scanning. Further, the second and third embodiments of the invention can be implemented with a medical imager having only one source and one detector, and acquiring only one image.

The invention claimed is:

1. Method for correcting an acquired medical image of a patient having an internal body structure, said acquired image having a region of interest showing a representation of said internal body structure, said acquired image having been acquired in a medical imager having a radiation source and a radiation detector spaced from one another along an image-taking direction, and between which the patient is disposed, wherein the method comprises:
   a) obtaining, via at least one computer processor, from the acquired image stored in a non-transient computer-readable information storage medium in operative connection with the at least one computer processor, a corrected image taking into account a position of the internal body structure along the image-taking direction, by:
      determining said position of the internal body structure along the image-taking direction,
      using said position of the internal body structure along the image-taking direction to calculate the magnification factor corresponding to said position,
      and resizing said acquired image according to said calculated magnification factor to obtain said corrected image.

2. Method according to claim 1, further comprising, prior to step a), the step b) of obtaining the position of the internal body structure along the image-taking direction via, at least, a positioning device of known geometric relationship with respect to said source and detector along said image-taking direction.

3. Method according to claim 1, wherein said acquired medical image is a first acquired medical image acquired along a first image-taking direction, and further comprising, prior to step a), the step b) of obtaining the position of the internal body structure along the first image-taking direction from a second acquired medical image of the patient, the second acquired image having a region of interest showing a representation of said internal body structure, the second image having been acquired along a second image-taking direction different from the first image-taking direction.

4. Method according to claim 3, wherein said first and second image-taking directions are orthogonal.

5. Method according to claim 1, further comprising, prior to step a), the step b) of obtaining the position of the internal body structure along the image-taking direction via, at least, measuring the position and orientation along the image-taking position of an auxiliary emitting device generating a light marker on the external surface of the patient, wherein the position and orientation of the auxiliary emitting device along the image-taking position is referenced with respect to the source.

6. Method according to 1, further comprising, prior to step a), the step b) of obtaining the position of the internal body structure along the image-taking direction via, at least, measuring the position of the internal body structure along the image-taking direction using a calibrated set of lines of the medical imager.

7. Method according to claim 1, wherein step a) includes calculating, via the at least one computer processor, a distance along the image-taking direction between a position of the source while acquiring the image and said position of the internal body structure, and using, via the at least one computer processor, a distance between said position of the source and a position of the detector while acquiring the image along the image-taking direction.

8. Method according to claim 1, wherein the acquired image is a bi-dimensional image extending along two directions orthogonal to the image-taking direction, and wherein step a) includes scaling, via the at least one computer processor, the acquired image along both said two directions.

9. Method according to claim 1, wherein the acquired image is a bi-dimensional image extending along two directions orthogonal to the image-taking direction, and wherein step a) includes scaling, via the at least one computer processor, the acquired image along only one of said two directions.

10. Method according to claim 1, wherein said internal body structure is a first internal body structure at a first position along said image-taking direction, wherein the patient has a second internal body structure, said acquired image having a second region of interest showing a representation of said second internal body structure, wherein, step a) comprises obtaining, via the at least one computer processor, from the acquired image, the corrected image also taking into account the second position of the second internal body structure along the image-taking direction, the first and second positions along the image taking direction being different from one another.

11. Method according to claim 1, wherein the corrected image obtained at step a) is a first corrected image of an internal body structure at a first position along the image-taking direction, the method further comprising the step a') of obtaining, via the at least one computer processor, from the acquired image, a second corrected image taking into account a second position of the internal body structure along the image-taking direction, the first and second positions being different from one another.

12. Method for reconstruction of a patient-specific three-dimensional model comprising:
   obtaining at least one corrected image of a patient using a method according to claim 1,
   obtaining a patient-specific three-dimensional model from said at least one corrected image and an a priori knowledge base of the internal body structure.

13. Method for measuring an anatomical geometrical parameter of an internal body structure of a patient comprising obtaining at least one corrected image of a patient using a method according to claim 1, and obtaining, via the at least one computer processor, the geometrical parameter from the corrected image.

14. A non-transient computer-readable information storage medium including a computer program product comprising instructions for causing a programmable unit to perform the method of claim 1, when executed on said programmable unit.

15. Method for medical imaging a patient comprising acquiring said acquired medical image of a patient in a medical imager having a radiation source and a radiation detector spaced along said image-taking direction, and between which the patient is disposed, and
   applying the method of claim 1 to said acquired image.

16. Method for medical imaging a patient according to claim 15, wherein acquiring said acquired medical image is performed by moving simultaneously said source and said detector along a scanning direction orthogonal to the image-taking direction.

17. Method for medical imaging a patient according to claim 15, wherein said acquired image is a first acquired image having been acquired by a first source and a first detector spaced along a first image-taking direction, the method further comprising acquiring a second acquired medical image of the patient with the medical imager having a second radiation source and a second radiation detector spaced along a second image-taking direction different from the first image-taking direction, and between which the patient is disposed, and
   obtaining the position of the internal body structure along the first image-taking direction from the second acquired image.

18. Method for medical imaging a patient according to claim 17, wherein acquiring said second acquired medical image is performed by moving simultaneously said second source and said second detector along a scanning direction orthogonal to the second image-taking direction.

19. Method for medical imaging a patient according to claim 17, wherein said first acquired image and said second acquired image are acquired simultaneously.

20. Medical imager comprising:
   a radiation source,
   a radiation detector spaced from the radiation source along an image-taking direction,
   a non-transient computer readable information storage medium including instructions that when executed by a computer processor operatively connected to the information storage medium obtain a corrected image from an acquired medical image of a patient with an internal body structure disposed between said source and detector, said acquired image having a region of interest showing a representation of said internal body structure, said corrected image taking into account a position of the internal body structure along the image-taking direction,
      said position of the internal body structure along the image-taking direction is determined
      said position of the internal body structure along the image-taking direction is used to calculate the magnification factor corresponding to said position,
      and said acquired image is resized according to said calculated magnification factor to obtain said corrected image.

21. Medical imager according to claim 20, further comprising a positioning device adapted for obtaining said position, the geometric relationship of the positioning device with respect to said source and detector being known.

22. Medical imager according to claim 21, wherein said radiation source is a first radiation source, said radiation detector is a first detector spaced from the first source along a first image-taking direction, and wherein the positioning device comprises a second radiation source and a second radiation detector spaced along a second image-taking direction, and between which the patient is disposed, the second image-taking direction being different from the first image-taking direction.

23. Medical imager according to claim 21, wherein the positioning device comprises an auxiliary emitting device of known relative position to the source and detector, said auxiliary emitting device being operable to emit a light marker visible on an external surface of the patient.

24. Medical imager according to claim 21, wherein the positioning device comprises a calibrated set of lines operable for measuring said position.

25. Method for correcting an acquired medical image of a patient having an internal body structure, said acquired image having a region of interest showing a representation of said internal body structure, said acquired image having been acquired in a medical imager having a radiation source and a radiation detector spaced from one another along an image-taking direction, and between which the patient is disposed, wherein the method comprises:

a) obtaining, via at least one computer processor, from the acquired image stored in a non-transient computer-readable information storage medium in operative connection with the at least one computer processor, a corrected image taking into account a position of the internal body structure along the image-taking direction, by:

determining said position of the internal body structure along the image-taking direction, using said position of the internal body structure along the image-taking direction to calculate the magnification factor corresponding to said position, and resizing said acquired image according to said calculated magnification factor to obtain said corrected image, and wherein said corrected image is a downsizing of said acquired image.

26. Method for correcting an acquired medical image of a patient having an internal body structure, said acquired image having a region of interest showing a representation of said internal body structure, said acquired image having been acquired in a medical imager having a radiation source and a radiation detector spaced from one another along an image-taking direction, and between which the patient is disposed, wherein the method comprises:

a) obtaining, via at least one computer processor, from the acquired image stored in a non-transient computer-readable information storage medium in operative connection with the at least one computer processor, a corrected image taking into account a position of the internal body structure along the image-taking direction, by:

determining said position of the internal body structure along the image-taking direction, using said position of the internal body structure along the image-taking direction to calculate the magnification factor corresponding to said position, and resizing said acquired image according to said calculated magnification factor to obtain said corrected image, and wherein said corrected image is an image in which the effect of said magnification factor on said acquired image has been cancelled.

* * * * *